United States Patent [19]
Krafft

[11] Patent Number: 5,492,671
[45] Date of Patent: Feb. 20, 1996

[54] STERILIZATION CASE AND METHOD OF STERILIZATION

[75] Inventor: Petrus Krafft, Warsaw, Ind.

[73] Assignee: Zimmer, Inc., Warsaw, Ind.

[21] Appl. No.: 359,979

[22] Filed: Dec. 20, 1994

[51] Int. Cl.$^6$ ................................................. A61L 2/00
[52] U.S. Cl. ........................... 422/26; 206/363; 206/370; 422/297; 422/300
[58] Field of Search .................... 422/292, 300, 422/297, 905, 26; 206/363, 369, 370, 478, 480, 483, 564, 565

[56] References Cited

U.S. PATENT DOCUMENTS

| | | | |
|---|---|---|---|
| D. 276,462 | 11/1984 | Villarreal | D24/31 |
| D. 321,249 | 10/1991 | Gorski | D24/229 |
| 682,522 | 9/1901 | Boekel et al. | |
| 746,999 | 12/1903 | Schmitz | |
| 2,880,865 | 4/1959 | Knox | 206/72 |
| 3,837,477 | 9/1974 | Boudreau | 206/72 |
| 4,135,868 | 1/1979 | Schainholz | 422/310 |
| 4,541,992 | 9/1985 | Jerge et al. | 422/300 |
| 4,705,168 | 11/1987 | Ward | 206/373 |
| 4,762,688 | 8/1988 | Berry, Jr. | 422/310 |
| 4,798,292 | 1/1989 | Hauze | 206/439 |
| 4,854,475 | 8/1989 | Riihimaki et al. | 220/337 |
| 4,959,199 | 9/1990 | Brewer | 422/300 |
| 5,046,624 | 9/1991 | Murphy et al. | 211/70.6 |
| 5,174,453 | 12/1992 | Stoeffler | 206/570 |
| 5,215,726 | 6/1993 | Kudla et al. | 422/297 |
| 5,340,551 | 8/1994 | Berry, Jr. | 422/300 |
| 5,346,075 | 9/1994 | Nichols et al. | 211/60.1 |
| 5,346,677 | 9/1994 | Risk | 422/297 |

*Primary Examiner*—Robert J. Warden
*Assistant Examiner*—Krisanne M. Thornton
*Attorney, Agent, or Firm*—Margaret L. Geringer

[57] ABSTRACT

A sterilization case 1 having one or more brackets 10 which are designed to enhance the steam sterilization of a medical apparatus 30 being held in the bracket 10. The bracket 10 is designed to provide cutout areas 51 to create a gap or gaps 52 between the surface of the apparatus 30 being held and the recess in the bracket 10, and yet still securely grip and hold the apparatus 30 in the bracket. The invention is adaptable to a wide variety of different shaped apparatus 30.

10 Claims, 3 Drawing Sheets 5,492,671

STERILIZATION CASE AND METHOD OF STERILIZATION

FIELD OF THE INVENTION

The invention relates to the field of sterilization cases. In particular, this invention relates to sterilization cases used for medical apparatus, and a method for enhancing such sterilization.

BACKGROUND OF THE INVENTION

It is well known in the medical industry, and in particular in the field of orthopaedics, to provide sterilization cases with brackets for securely holding parts to prevent the parts from moving around in the case and contacting other parts during transportation and sterilization. This protects the parts from damage and keeps them organized. Typically, these bracket designs have simple u-shaped recesses or recesses which conform to the shape of the part being held. Such conforming-shaped recesses tend to shield the surface of the part which is held by the recess and can inhibit steam penetration/circulation about that surface of the part during steam sterilization.

SUMMARY OF THE INVENTION

The present invention provides a sterilization case having one or more brackets which are designed to enhance steam sterilization of the part or parts being held in the bracket. The bracket of the present invention is designed to provide cutout areas to create a gap or gaps between the surface of the part or apparatus being held and the recess in the bracket, and yet still securely grip and hold the part in the bracket.

Accordingly, it is an advantage of the invention to provide a bracket for a sterilization case which will securely hold a medical apparatus or part to be sterilized, while enhancing the sterilization of the part by increasing the ability of steam to circulate about the part during the steam sterilization process.

Another advantage of this invention is to provide a simple method for enhancing the steam sterilization of a medical apparatus or medical components which can be easily adapted to various shaped parts.

Still other advantages of the invention will become apparent upon reference to the accompanying drawings.

DESCRIPTION OF THE PREFERRED EMBODIMENT

Figure 1:
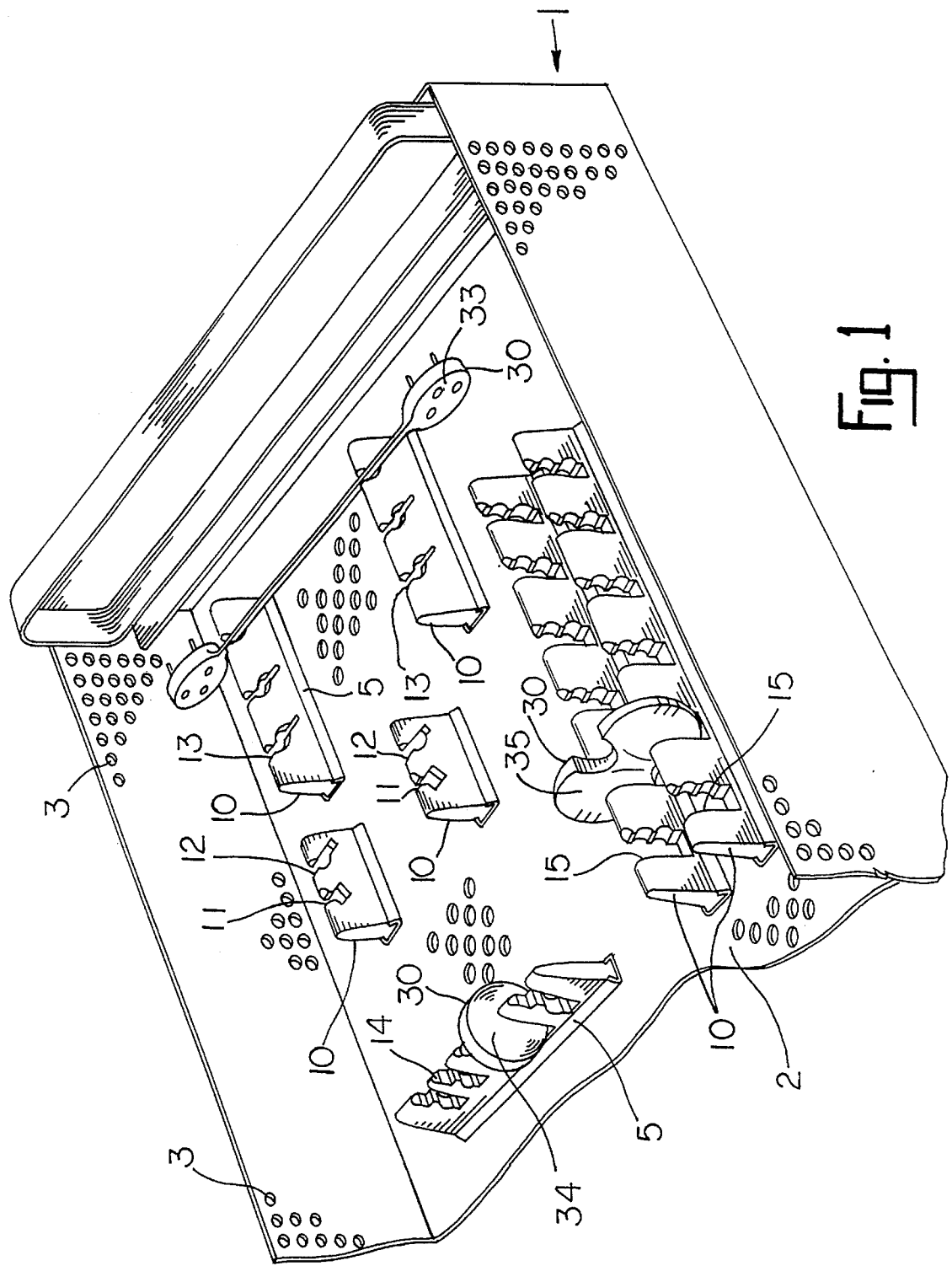
FIG. 1 is a perspective view of a portion of a sterilization case including various brackets and medical apparatus therein in accordance with the present invention.
Figure 2:
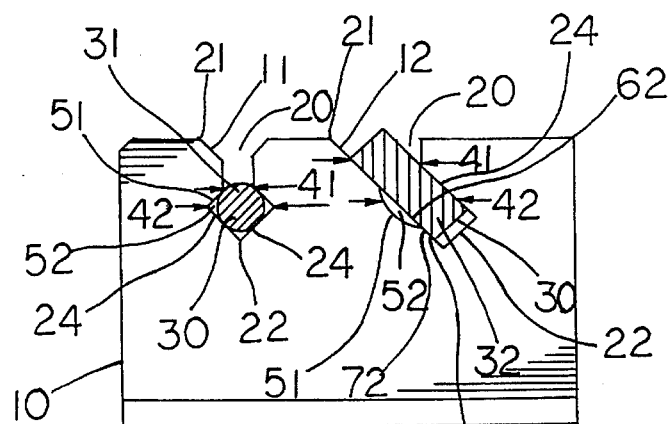
FIG. 2 is a side elevational view of one of the brackets of FIG. 1 with a cross-sectional view of two different medical apparatus being held by the bracket.
Figure 3:
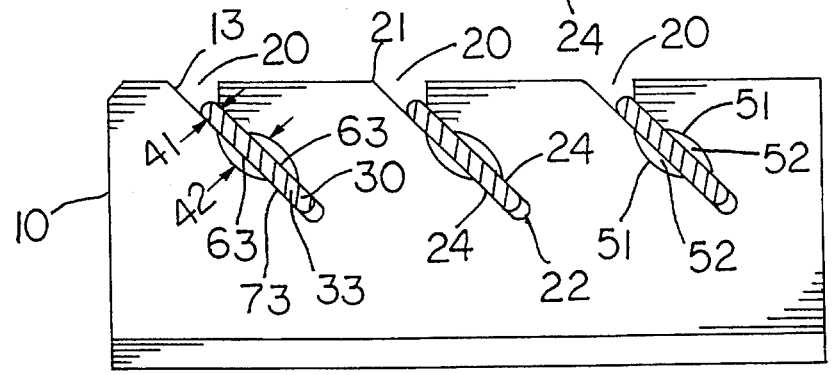
FIG. 3 is a side elevational view of another one of the brackets of FIG. 1 with a cross-section view of another medical apparatus being held by the bracket.
Figure 4:
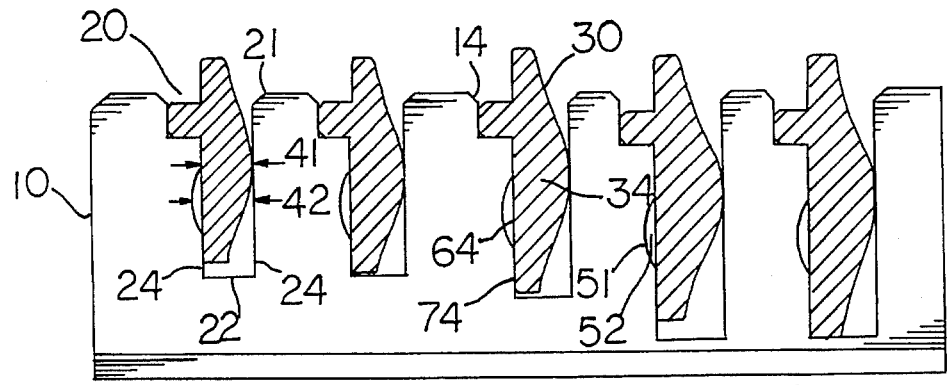
FIG. 4 is a side elevational view of a further one of the brackets of FIG. 1 with a cross-sectional view of a further medical apparatus being held by the bracket.
Figure 5:
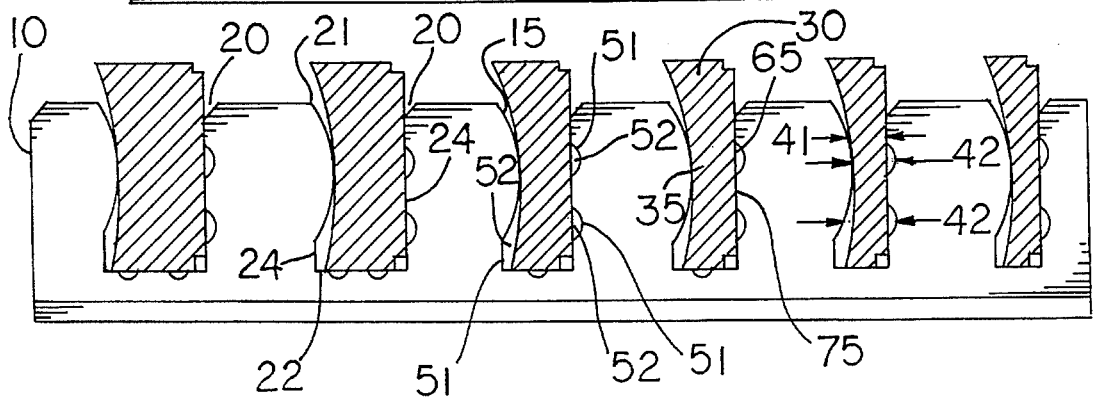
FIG. 5 is a side elevational view of a still further one of the brackets of FIG. 1 with a cross-sectional view of a still further medical apparatus being held by the bracket.

The preferred embodiment described herein is not intended to be exhaustive or to limit the invention to the precise form disclosed. Rather it is chosen and described to best explain the invention so that others skilled in the art might utilize its teaching.

Accordingly, FIGS. 1–5 illustrate the preferred embodiment of a steam sterilization case 1 with various medical apparatus 30 securely held therein in the brackets 10 in accordance with the present invention. The sterilization case may include a base portion 2 and a corresponding lid or cover portion (not shown). The sterilization case also includes a plurality of holes 3 therethrough as is well known for use on sterilization cases. The base portion 2 includes a plurality of holding brackets 10 extending from base portion 2. The brackets 10 include substantially U-shaped recesses 11,12,13,14,15, each having varying shapes to accommodate varying shapes and sizes of medical apparatus 30, such as 31,32,33,34,35. The medical apparatus 30 may be any suitable devices including various instrumentation, provisionals or trial components for orthopaedic implants, and orthopaedic implants. Each recess 11,12,13,14,15 has an opening 20 at a first end 21 for receiving the corresponding medical apparatus 30 and an oppositely located second end 22 and two oppositely facing walls 24 interconnecting the first and second ends 21,22. The two oppositely facing walls 24 of recesses 11,12,13,14,15 have a first width 41 therebetween for tightly contacting and securely gripping a portion of the corresponding apparatus therebetween. Each recess 11,12,13,14,15 includes one or more cutouts 51 located between the first width 41 and the second end 22 for enlarging the recess 11,12,13,14,15 and creating one or more gaps 52 between the corresponding apparatus 30 and at least one of the oppositely facing walls 24 to enhance the steam circulation around the apparatus during the steam sterilization process of the apparatus.

The cutouts 51 provide a second width 42 between oppositely facing walls 24 which is larger than first width 41. The cutouts 51 may be U-shaped or of various other shapes and sizes depending upon the shape of the apparatus 30 and the shape desired for gap 52.

This invention is particularly suitable for a medical apparatus 30, such as items 32,33,34, and 35, which each have at least one substantially planar surface 62,63,64, and 65, respectively. This substantially planar surface 62,63,64, or 65 may abut or mate with a corresponding substantially planar surface 72,73,74, and 75, respectively, of at least one of the oppositely facing walls 24 in recesses 12,13,14, and 15, respectively. Accordingly, the gap 52 created by the cutout 51 in surface 72,73,74, or 75 is provided along a portion of the substantially planar surface 62,63,64, or 65 of the medical apparatus 32,33,34,or 35, respectively.

The brackets 10 are preferably made from a non-metallic material, such as silicone, in order to provide some flexibility for inserting the varying shaped apparatus 30 into correspondingly shaped recesses, such as 11,12,13,14,15 for securely holding and gripping the apparatus. It is known in the art to make sterilization brackets from silicone. The shapes of the recesses may be varied in accordance with the invention to accommodate any suitably shaped apparatus.

The sterilization case 1 is typically made of metal, such as aluminum or stainless steel. The brackets 10 may be secured to the base portion 2 of the case 1 in any suitable manner. In the embodiment shown, bracket 10 is held in a metal bracket holding strip 5. This assembly is suitably secured to the base portion 2. The brackets may also be arranged in the case in any desirable manner. It is noted that a medical apparatus 30 may be held by a single bracket 10, such as with item 34, or may be held by more than one bracket combination, such as with items 33 and 34.

Figure 6:
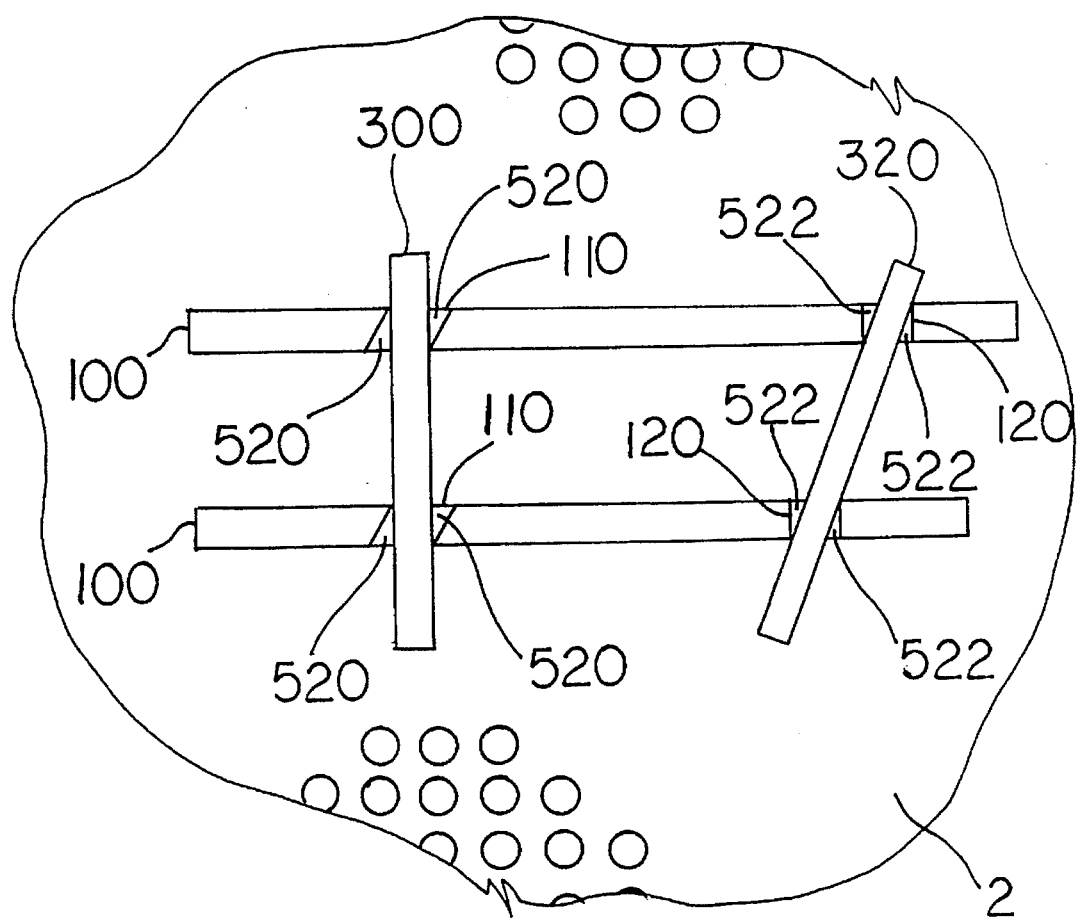
FIG. 6 is a top view of an alternate pair of brackets showing an alternate embodiment.

In an alternate embodiment shown in FIG. 6, it is noted that recesses 110 in brackets 100 may be cut at an angle instead of perpendicular to the silicone brackets 100. The pair of recesses 110 in the two brackets 100 are aligned across from each other. The embodiment creates gaps 520 between the recesses 110 and the straight edged apparatus 300 as shown. Alternatively, two recesses 120 which are cut perpendicularly to brackets 100 may be offset across from each other so that the recesses 120 are set at an angle to each other to create gaps 522 between the recesses 120 and a straight edge apparatus 320 set therein. The opposite corner edges of recesses 110 and 120 contact the apparatus 300 and 320 to grip and securely hold the apparatus 300 and 320.

While this invention has been described in terms of a particularly advantageous embodiment, those skilled in the art can appreciate that modifications can be made without departing from the spirit and scope of this invention.

I claim:

1. A combination comprising, a steam sterilization case and a medical apparatus for being securely held in the sterilization case, wherein the sterilization case includes a base portion with at least one holding bracket extending from the base portion, and wherein the at least one bracket includes a recess defined by an opening at a first end for receiving the medical apparatus and an oppositely located second end and two oppositely facing walls interconnecting the first and second ends, and wherein the two oppositely facing walls of the recess have a first width therebetween for contacting and securely gripping a portion of the medical apparatus therebetween, and wherein the recess includes a cutout means located between the first width of the recess and the second end of the recess for enlarging the recess and creating a gap between the medical apparatus and at least one of the oppositely facing walls of the recess to enhance the steam circulation around the medical apparatus during steam sterilization of the medical apparatus.

2. The combination of claim 1 wherein the cutout means provides a second width between the oppositely facing walls of the recess which is larger than the first width.

3. The combination of claim 1 wherein the cutout means creates a plurality of gaps between the medical apparatus and the recess.

4. The combination of claim 1 wherein the at least one of the oppositely facing walls includes a substantially planar surface which mates with a corresponding substantially planar surface on the medical apparatus, and wherein the gap created by the cutout means is provided along a portion of said substantially planar surface of the medical apparatus.

5. The combination of claim 1 wherein the at least one bracket is made from a non-metallic material.

6. A method of enhancing sterilization comprising the following steps:

a) providing a medical apparatus and a steam sterilization case, the case having a base portion with at least one holding bracket extending from the base portion;

b) providing the at least one bracket with a recess defined by an opening at a first end for receiving the medical apparatus and an oppositely located second end and two oppositely facing walls interconnecting the first and second ends;

c) providing the two oppositely facing walls of the recess with a first width therebetween for contacting and securely gripping a portion of the medical apparatus therebetween;

d) providing the recess with a cutout means located between the first width of the recess and the second end of the recess for enlarging the recess and creating a gap between the medical apparatus and at least one of the oppositely facing walls of the recess to enhance the steam circulation around the medical apparatus during steam sterilization of the medical apparatus.

7. The method of claim 6 wherein the method further includes the step of providing the cutout means with a second width between the oppositely facing walls of the recess which is larger than the first width.

8. The method of claim 6 wherein the method further includes the step of providing the cutout means such that the cutout means creates a plurality of gaps between the medical apparatus and the recess.

9. The method of claim 6 wherein the method further includes the step of providing the at least one of the oppositely facing walls with a substantially planar surface to mate with a corresponding substantially planar surface on the medical apparatus, and thus, providing the gap created by the cutout means alongside a portion of said substantially planar surface of the medical apparatus.

10. The method of claim 6 wherein the method further includes the step of manufacturing the at least one bracket from a nonmetallic material.

* * * * *